United States Patent [19]
Desantis

[11] Patent Number: 5,965,772
[45] Date of Patent: Oct. 12, 1999

[54] PROCESS FOR THE PREPARATION OF 5-(ACETYL(2,3-DIHYDROXYPROPYL)AMINO-N,N-BIS(2,3-DIHYDROXYPROPYL)-2,4,6-TRIIODO

[75] Inventor: Nicola Desantis, Cernvsco, Italy

[73] Assignee: Dibra S.p.A., Italy

[21] Appl. No.: 09/084,922

[22] Filed: May 28, 1998

[30] Foreign Application Priority Data

May 30, 1997 [IT] Italy .................................. MI97A1268

[51] Int. Cl.$^6$ .................................. C07C 233/05
[52] U.S. Cl. ........................ 564/153; 424/9.452; 562/855; 562/142
[58] Field of Search .................................. 564/153, 142; 424/9.452; 562/855

[56] References Cited

U.S. PATENT DOCUMENTS

| | | | |
|---|---|---|---|
| 4,001,323 | 1/1977 | Felder et al. | 424/5 |
| 4,250,113 | 2/1981 | Nordal et al. | 564/153 |
| 5,616,795 | 4/1997 | Mauro et al. | 562/855 |

OTHER PUBLICATIONS

Haavaldsen et al, Acta Pharm. Suec., 20, pp. 219–232, 1983.

*Primary Examiner*—Shailendra Kumar
*Attorney, Agent, or Firm*—Nixon & Vanderhye

[57] ABSTRACT

A process for the preparation of 5-[acetyl(2,3-dihydroxypropyl)amino]-N,N'-bis(2,3-dihydroxypropyl)-2,4,6-triiodo-1,3-benzenedicarboxamide of formula (I), starting from 5-amino-1,3-benzenedicarboxylic acid of formula (II), comprising the following steps:

step a) is the reaction in heterogeneous phase between 5-amino-2,4,6-triiodo-1,3-benzenedicarboxylic acid and thionyl chloride in a solvent selected from the group consisting of: straight or branched ($C_7$–$C_{16}$) hydrocarbons, ($C_7$–$C_8$) aromatic hydrocarbons, 1,1,1-trichloroethane, n-butyl acetate, diglyme (diethylene glycol dimethyl ether), in the presence of catalytic amounts of a tertiary amine, to give compound (III);

step b) is the acetylation reaction of compound (III) with glacial acetic acid both as the solvent and the reagent and thionyl chloride;

step c) is the formation of compound (V) by reaction of the compound (IV) with 1-amino-2,3-propanediol, by reaction of compound (IV) in a dipolar aprotic solvent, selected from the group of dimethylformamide (DMF), dimethylacetamide (DMA), dimethylsulfoxide (DMSO) or N-methyl-pyrrolidinone;

step d) is the alkylation of the compound (V) in aqueous solution at basic pH, by addition of a sodium hydroxide-calcium hydroxide mixture, with 3-chloro-1,2-propanediol or epichlorohydrin, at a temperature of 40–90° C.

15 Claims, No Drawings

PROCESS FOR THE PREPARATION OF 5-(ACETYL(2,3-DIHYDROXYPROPYL)AMINO-N,N-BIS(2,3-DIHYDROXYPROPYL)-2,4,6-TRIIODO

The present invention relates to a novel process for the preparation of 5-[acetyl(2,3-dihydroxypropyl)amino]-N,N'-bis(2,3-dihydroxypropyl)-2,4,6-triiodo-1,3-benzenedicarboxamide of formula (I), more commonly known under the name Iohexol, one of the most widely used non-ionic X-ray contrast agents, starting from the compound of formula (II), 5-amino-2,4,6-triiodo-1,3-benzenedicarboxylic acid.

The preparation of the compound of formula (I) was first described in GB 1,548,594, starting from 5-nitro-1,3-benzenedicarboxylic acid methyl diester, according to the following Scheme 1.

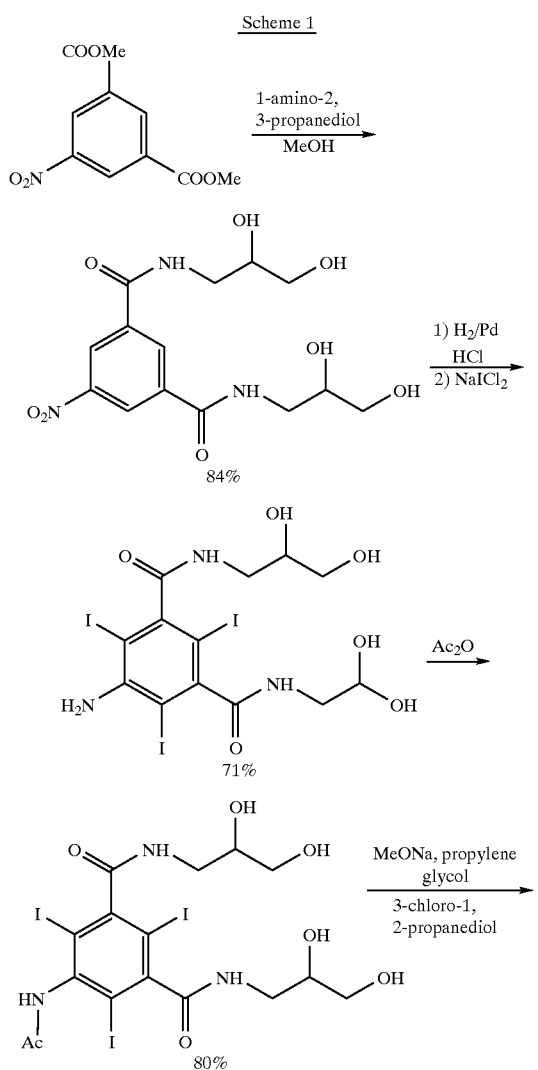

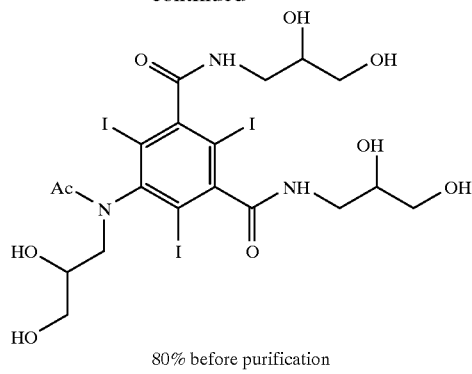

80% before purification

This synthetic approach was subsequently compared with an alternative one in a more recent paper (Haavaldsen et al, Acta Pharm. Suec., 20, 219, 1983) starting from a different substrate, namely the compound of formula (III), 5-amino-2,4,6-triiodo-1,3-benzenedicarboxylic acid dichloride, according to the following Scheme 2.

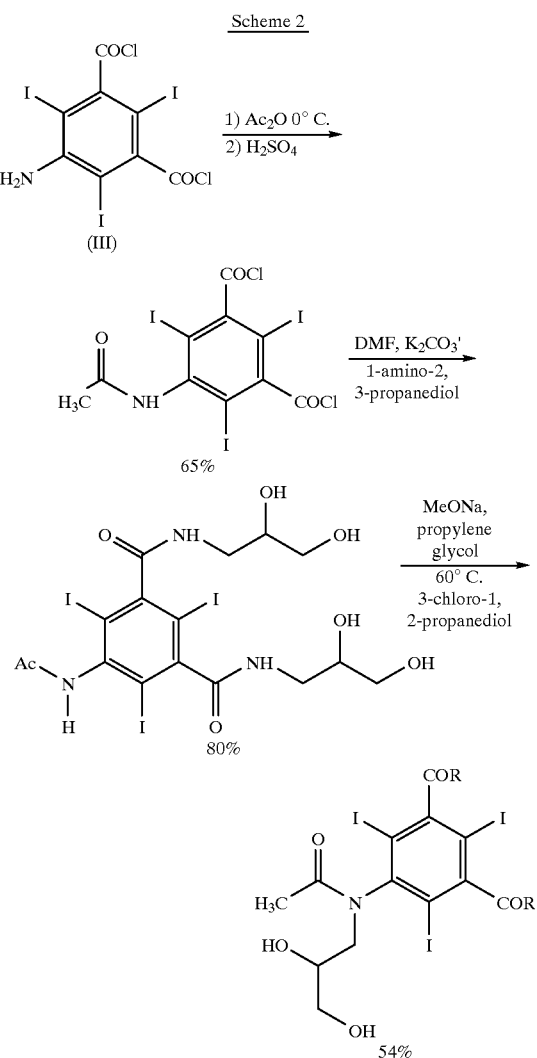

According to what stated in this paper, the compound of formula (III), 5-amino-2,4,6-triiodo-1,3-benzenedicarboxylic acid dichloride, is prepared following the procedure disclosed in U.S. Pat. No. 4,001,323, and is subjected to an acetylation reaction in acetic anhydride at low temperature, giving a 65% yield in the final product.

The synthesis subsequently includes the formation of the amides of the acidic groups at the 1- and 3-positions with 1-amino-2,3-propanediol (commonly namely isoserinol), with an 80% declared yield. The final step involves the alkylation of the amido nitrogen at the 5-position 5 with 3-chloro-1,2-propanediol, in propylene glycol by means of sodium methoxide, to give the final product, after a troublesome purification, in a 54% yield.

The comparison with the process described in the above Patent evidences that only the latter is the most industrially suitable preparation, this being also confirmed by the review concerning Iohexol published in Farmakoterapi (T. Jacobsen, 1982, 45–57), considering the better yields in the single steps and the reduced number of the involved steps.

Recently, U.S. Pat. No. 5,616,795 disclosed a very efficient synthesis of 5-amino-2,4,6-triodo-1,3-benzenedicarboxylic acid dichloride, comprising the reaction in heterogeneous phase between 5-amino-2,4,6-triiodo-1,3-benzenedicarboxylic acid and thionyl chloride, in a solvent selected from the group consisting of: straight or branched ($C_7$–$C_{16}$) hydrocarbons, ($C_7$–$C_8$) aromatic hydrocarbons, 1,1,1-trichloroethane, n-butyl acetate, diglyme (diethylene glycol dimethyl ether), in the presence of catalytic amounts of a tertiary amine.

The synthetic procedure disclosed in this Patent made it possible to remarkably improve the yields of the single steps from the industrial point of view, compared with the process described in the Patent used by Haavaldsen for the preparation of the compound of formula (III) cited above, i.e. U.S. Pat. No. 4,001,323.

It has now been found a process starting from the compound of formula (II), involving the formation of the compound of formula (III) which, contrary to the prior art teachings, leads to the final product efficiently and economically from the industrial point of view.

It is therefore the object of the present invention a novel process for the preparation of the compound of formula (I) starting from 5-amino-1,3 -benzenedicarboxylic acid, comprising the following steps represented in Scheme 3:

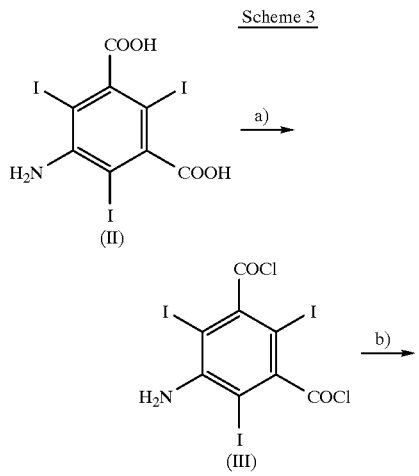

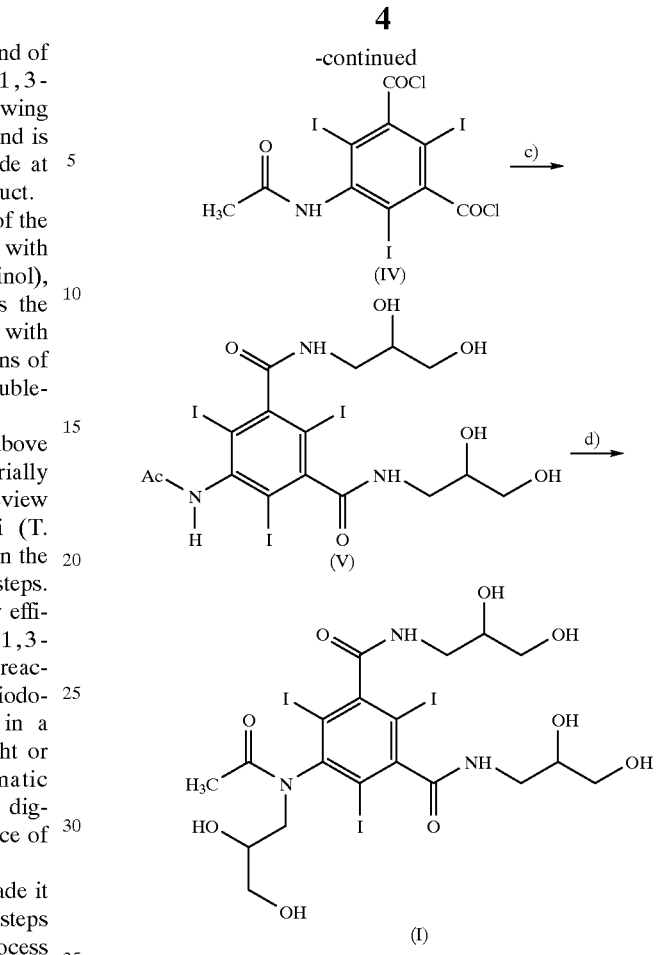

in which step a) is the reaction in heterogeneous phase between 5-amino-2,4,6-triiodo-1,3-benzenedicarboxylic acid and thionyl chloride in a solvent selected from the group consisting of: straight or branched ($C_7$–$C_{16}$) hydrocarbons, ($C_7$–$C_8$) aromatic hydrocarbons, 1,1,1-trichloroethane, n-butyl acetate, diglyme (diethylene glycol dimethyl ether), in the presence of catalytic amounts of a tertiary amine, to give compound (III);

step b) is the acetylation reaction of compound (III), using two procedures:
glacial acetic acid both as the solvent and the reagent and thionyl chloride, or, alternatively,
acetyl chloride in a dipolar aprotic solvent;

step c) is the formation of compound (V) by reaction of the compound (IV) with 1-amino-2,3-propanediol, using two procedures:
reaction of compound (IV) in a dipolar aprotic solvent, with an isoserinol amount 4.2–4.6 times the moles of compound (IV); or, alternatively,
reaction of compound (IV) in a dipolar aprotic solvent, in the presence of an amount of a tertiary amine, with an isoserinol amount 2.05–2.4 times the moles of compound (IV);

step d) is the alkylation of the compound (V) in aqueous solution at basic pH, by addition of a sodium hydroxide and calcium hydroxide mixture, with 3-chloro-1,2-propanediol or epichlorohydrin, at a temperature of 40–90° C.

Step a) is effected according to the procedure disclosed in U.S. Pat. No. 5,616,795 which provides high yields of compound of formula (III). The process of the present invention can thereby be advantageous from the industrial point of view, compared with that described in GB 1,548,594.

Particularly preferred are the following chlorination conditions:
the hydrocarbon is selected from the group of straight or branched ($C_8$–$C_{14}$) hydrocarbons, preferably n-octane, n-decane, n-dodecane, ligroin, kerosene;
the aromatic hydrocarbon is selected from the group of the methyl-substituted benzenes, preferably toluene and xylenes;
the tertiary amine is selected from the group of N-methylmorpholine, triethylamine, quinoline, dimethylaminopyridine, 2-ethyl-5-methylpyridine.

The addition of diglyme, in amounts from 0.5 kg of diglyme/kg of starting product, to the 5-amino-2,4,6-triiodo-1,3-benzenedicarboxylic acid chlorination mixture and the subsequent treatment with water, involve a remarkably advantage in the work up of such reaction, allowing to recover the final product in high yields and purity.

A synthetic process providing the final product in high yields, under safe operative conditions, and with a suitable purity for use in the subsequent steps without further purifications (crystallization, etc.) is very valuable from the industrial point of view.

A preparation of compound (III) using n-dodecane and quinoline as tertiary amine will be described by way of example in the experimental section.

Step b) is the acetylation reaction of compound (III) which is carried out, in an innovative way, using two procedures:
1. glacial acetic acid both as the solvent and the reagent and thionyl chloride at a temperature of 50–60° C.
The amount of AcOH is preferably 40–60 times the moles of compound (III).
Thionyl chloride is preferably present in amounts 2–4 times the moles of compound (III).
The reaction time is of 3–4 hours.
At the end of the reaction, the precipitated product is collected by filtration. According to this method it is also possible to distil to dryness the acetylating mixture at the end of the reaction, thereby recovering the product.
Thus, the distillate can conveniently be recycled in the industrial process;
2. acetyl chloride in a dipolar aprotic solvent, selected from the group of dimethylformamide (DMF), dimethylacetamide (DMA), dimethylsulfoxide (DMSO) or N-methylpyrrolidinone, at a temperature of 0–40° C.
Acetyl chloride is added in amounts 1.5–3 times the moles of compound (III).
The reaction time is in this case 35–65 hours.
The desired product is recovered by dropping the final reaction mixture into ice-water to precipitate the product which is collected by filtration.
The yields obtained with both procedures range from 88 to 98%, therefore remarkably improving the yields of this step compared with that described by Haavaldsen, providing at the same time a high quality product (see the experimental section) without need for further purifications.

Step c) is the reaction of formation of the isoserinol amides of compound (IV), which is carried out in two ways:
1. reaction of compound (IV) in a dipolar aprotic solvent, preferably DMF and DMA, with an isoserinol amount 4.2–4.6 times the moles of compound (IV);
2. reaction of compound (IV) in a dipolar aprotic solvent, preferably DMF and DMA, in the presence of an aliphatic tertiary amine, selected from the group of: triethylamine, tributylamine, tripropylamine, trimethylamine, N-methylmorpholine, preferably triethylamine and tripropylamine, with an isoserinol amount 2.05–2.4 times the moles of compound (IV).

The yields obtained in this step vary from 90 to 98%, for both procedures used.

The step of formation of the amides of the present invention, in addition to the high yield, involves a further advantage compared with that by Haavaldsen, in that the acid-binding agent is in homogeneous phase instead of being an inorganic salt.

Both procedures make it possible to recover the isoserinol excess or the tertiary amine used as a catalyst, except for triethylamine, by use of ion exchange resins at the end of the amidation reaction. On the contrary, in the case of triethylamine it is more convenient to filter the hydrochloride formed during the reaction and then to recover the amine by simple basic hydrolysis.

Step d) is the alkylation which can be surprisingly carried out in aqueous medium, alkalinized by addition of a sodium hydroxide-calcium hydroxide mixture, in a sodium hydroxide to compound (V) equimolar ratio and in a calcium hydroxide to compound (V) ratio of 0.5–0.9, always keeping pH at 10–12, at a temperature of 40–90° C.

The reaction time ranges from 30 min. to 4 h.

The compound (V) is suspended in water and heated to the suitable temperature.

Sodium hydroxide is then added until complete dissolution, then calcium hydroxide is added, which remains in part as a precipitate.

Unexpectedly, the addition of calcium hydroxide proved to be of paramount importance. The reaction, in fact, when carried out in the presence of only sodium hydroxide, gave a lower yield (max. 52%) and a by-products.

A 10–20% aqueous solution of the alkylating agent is added at the same temperature as above. The reaction is very rapid, providing the maximum yield 30 min. after the end of the addition. The reaction is quenched by addition of glacial acetic acid.

The progress of the reaction was monitored using the analytic procedures reported in the XXIII US Pharmacopoeia (USP, Ed. 1995, page 825). The yield of the alkylation step is of 80–95%.

The final solution is purified through a battery of strong cationic ion exchange resins (such as Amberjet 1200 or Amberlite IR120), followed by an anionic one (medium or strong, such as Amberlite IRA 420 or Relite MG1), optionally followed by a column of reduced size containing a strong cationic resin as defined above.

Such purification mainly removes salts, such as NaCl, $Ca(OAc)_2$ and ionic by-products.

The eluate is further passed through a styrene matrix macroporous resin (such as Amberlite or Amberlite XAD 1600, XAD 16) or silica matrix "reverse-phase" resins (such as RP-18, RP-10). Water is evaporated off under vacuum, then a $C_2$–$C_4$ alcohol is added (preferably ethanol or n-butanol) to precipitate the final crystalline product, which needs no further recrystallizations, as it is of the same quality as reported in US Pharmacopoeia.

Contrary to what suggested by the literature concerning the preparation of Iohexol, wherein the alkylation reaction carried out in propylene glycol with sodium methoxide as base was always preferred, the Applicant obtained results comparable to, or even better than, the preceding ones, and at the same time of lower environmental impact, as use is made of water as the solvent and of simple inorganic salts as base.

The following examples further illustrate the best experimental conditions to carry out the process of the invention.

EXPERIMENTAL SECTION

EXAMPLE 1

5-Amino-2,4,6-triiodo-1,3-benzenedicarboxylic acid dichloride

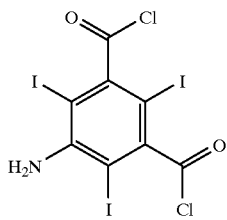

A mixture of 1.2 kg of 5-amino-2,4,6-triiodo-1,3-benzenedicarboxylic acid (prepared according to the procedure described in J. Org. Chem., 1994, 59, 1344), 6 g of quinoline and 970 g of dodecane is heated to 65–70° C., with stirring and under nitrogen atmosphere. After that, 500÷600 g of a $SOCl_2$/n-dodecane mixture containing 10% of the latter are added in 2 h, then, in 4÷6 h, 1 kg of $SOCl_2$, keeping the temperature from 65 to 70° C. At the end of the addition, the mixture is heated to 80÷85° C. in 2 h, keeping this temperature for 6 h, to complete the reaction. The mixture is then cooled at 40÷50° C., then heated to 80÷85° C. under vacuum, distilling a $SOCl_2$/n-dodecane mixture containing 10% of the latter, which can be recycled.

After that, pressure is brought to normal values by means of nitrogen, the reaction is cooled to a temperature lower than 55° C., and 1.1 kg of diglyme are added, under nitrogen atmosphere and with stirring, keeping the temperature at 40÷50° C.

280÷240 g of NaOH (13÷15% aqueous solution) are then added, temperature spontaneously rising to about 60° C., to reach a final pH of 2.5÷3. 300 g of water are subsequently added, pH is adjusted to 6 with 690÷590 g of NaOH (13÷15% aqueous solution) and finally the mixture is further diluted with 150÷180 g of water, cooling at 30° C.

The suspension is filtered under nitrogen atmosphere and the humid product is washed with water to neutral washings (pH 7).

The product is dried at 50÷65° C., to obtain 1.237 kg of the desired product.
Yield calculated on the dry product: 95.6%
$H_2O$ content: 1%
HPLC titre: 98.5%
Stationary phase: column E. Merck Lichrospher$^{(R)}$ RP-18 5 μm 4 mm×12.5 cm
Mobile phase: gradient elution
A=water
B=$CH_3CN$

| min | % B |
|---|---|
| 0 | 60 |
| 3 | 60 |
| 12 | 80 |
| 19 | 80 |
| 20 | 60 |
| Flow: | 1.2 ml min$^{-1}$ |
| Temperature: | 30° C. |
| Detection (UV): | 240 nm |

The $^1$H-NMR, $^{13}$C-NMR, IR and MS spectra are consistent with the indicated structure.

EXAMPLE 2

Preparation of 5-acetylamino-2,4,6-triiodo-1,3-benzenedicarboxylic acid dichloride

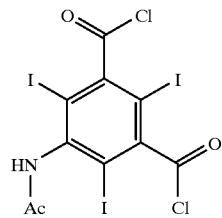

100 g of 5-amino-2,4,6-triiodo-1,3-benzenedicarboxylic acid dichloride (0.168 mol) are suspended in 500 g of glacial acetic acid at 60° C. 60 g of $SOCl_2$ (0.50 mol) are slowly added. The reaction ends after 3 hours. After cooling, the formed precipitate is recovered by filtration. The residue is washed first with acetic acid, then with water. Further precipitate is recovered from mother liquors and combined with the first one. 100 g of the desired product are obtained.
Yield: 93.4%
HPLC titre: 94.6%
Column Lichrospher RP-18 Merck; 12.5 cm×4 mm; 5 micron
Eluent: A $H_2O$
B $CH_3CN$

| Gradient | t (min) | % B |
|---|---|---|
| | 0 | 48 |
| | 3 | 48 |
| | 9.5 | 100 |
| | 15 | 100 |
| Flow | 1 mL/min | |
| Temperature | 30° C. | |
| Detection | 245 nm | |

EXAMPLE 3

Alternative method to that described in example 2

297.8 g of 5-amino-2,4,6-triiodo-1,3-benzenedicarboxylic acid dichloride (0.5 mol) are dissolved in 701 ml of DMAC at 5° C. 55 g of acetyl chloride (0.7 mol) are dropped into the solution, keeping the same temperature. At the end of the addition temperature raises to 18° C. After 24 h, further 10 g (0.013 mol) of acetyl chloride are added. The reaction ends after 52 hours. The solution is dropped into 3.7 kg of ice-water in 30 min, at a temperature below 5° C., stirring for about 30 min. The mixture is centrifuged and washed with 2 L of water, to obtain 612 g of the desired product.
Yield: 89.0%
HPLC titre: 97.7%

EXAMPLE 4

Preparation of 5-(acetylamino)-N,N'-bis(2,3-dihydroxypropyl)-2,4,6-triiodo-1,3-benzenedicarboxamide

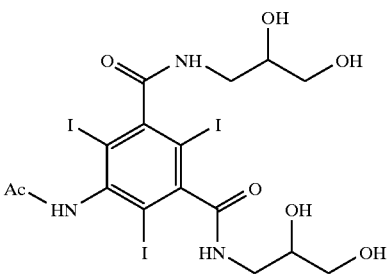

370.4 g (0.58 mol) of 5-acetylamino-2,4,6-triiodo-1,3-benzenedicarboxylic acid dichloride, prepared according to Example 1 or 2, are dissolved in 741.0 g of DMA. 232.8 g (2.6 mol) of 1-amino-2,3-propanediol are dissolved separately in DMA, then dropped into the 5-acetylamino-2,4,6-triiodo-1,3-benzenedicarboxylic acid dichloride solution in two hours at 0° C. The reaction is completed in 7 hours at 25° C.

DMA is distilled to dryness under a 12 mmHg vacuum at 92° C. After cooling to 50° C., the residue is taken up in 950.0 g of methanol and 500.0 g of water.

The mixture is adjusted to pH 10.5 by means of a 7% (w/w) sodium hydroxide solution, which is added repeatedly to steady pH 10.5, to obtain a solution of 5-(acetylamino)-N,N'-bis(2,3-dihydroxypropyl)-2,4,6-triiodo-1,3-benzenedicarboxamide sodium salt.

Precipitation of the product and recovery of 1-amino-2.3-propanediol.

The solution is cooled at room temperature and 36% (w/w) hydrochloric acid is added until pH 1.0. The precipitated product is filtered and dried.
Yield: 92%
HPLC titre: 98.4%
Column Lichrospher RP-18 Merck; 25 cm×4 mm; 5 micron
Eluent: A $H_2O$
B MeOH 25% (v/v) in water

| Gradient | t (min) | % B |
|---|---|---|
| | 0 | 7.5 |
| | 6 | 7.5 |
| | 18 | 35 |
| | 30 | 92 |
| | 34 | 92 |
| Flow | 1.5 mL/min | |
| Temperature | 35° C. | |
| Detection | 240 nm | |

Mother liquors are concentrated to dryness taken up with 500.0 g of water and then percolated onto 2000 ml of Amberjet 1200 cationic resin in the $Na^+$ form.

1-Amino-2,3-propanediol is then recovered by elution with a 7% (w/w) ammonia solution.

EXAMPLE 5

Alternative method to that described in Example 3
370.4 g (0.58 mol) of 5-acetylamino-2,4,6-triiodo-1,3-benzenedicarboxylic acid dichloride, prepared according to Example 1 or 2, are dissolved in 741.0 g of DMA, this solution is added with 122.0 g (1.20 mol) of 100% (w/w) triethylamine. 109.32 g (1.2 mol) of 1-amino-2,3-propanediol are dissolved separately in DMA and dropped into the first solution in two hours at 0° C. The reaction is completed in 7 hours at 25° C. Triethylamine hydrochloride precipitated during the amidation reaction is filtered off.

DMA is distilled to dryness under a 12 mmHg vacuum at 92° C. After cooling to 50° C., the residue is taken up in 950.0 g of methanol and 500.0 g of water.

The mixture is adjusted to pH 10.5 by means of a 7% (w/w) sodium hydroxide solution, which is added repeatedly until steady pH 10.5, to obtain a solution of N,N'-bis(2,3-dihydroxypropyl)-5-(acetylamino)-2,4,6-triiodo-1,3-benzenedicarboxamide sodium salt.

Precipitation of the product.

The solution is cooled at room temperature and 36% (w/w) hydrochloric acid is added until pH 1.0. The precipitated product is filtered and dried.
Yield: 96%
Total by-products: 1.4%

EXAMPLE 6

Preparation of 5-[acetyl(2,3-dihydroxypropyl)amino]-N,N'-bis(2,3-dihydroxypropyl)-2,4,6-triiodo-1,3-benzenedicarboxamide

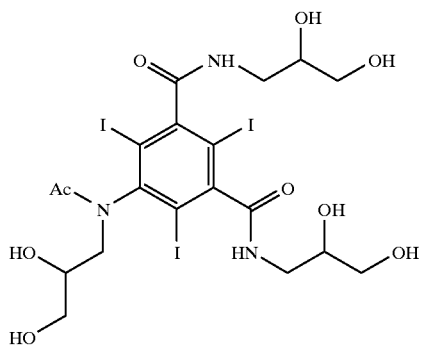

67.1 g (0.089 mol) of 5-(acetylamino)-N,N'-bis(2,3-dihydroxypropyl)-2,4,6-triiodo-1,3-benzenedicarboxamide (prepared as described in Example 4) are dissolved in 178.9 g of water and heated to 85° C. 44.73 ml of NaOH 2N (0.089 mol) and 4.83 g of Ca(OH)$_2$ (0.065 mol) are added at said temperature. After 30 min, a solution of 13.42 g (0.12 mol) of 3-chloro-1,2-propanediol in 79.33 g of water is dropped therein, keeping the same temperature for a further 30 min.

The reaction is quenched with acetic acid until solubilization. After that, the solution is percolated on a ion exchange resin (Amberjet 1200. 400 mL, IRA 420 150 mL, Amberjet 1200 50 mL). The eluate is then percolated on 200 ml of Amberlite XAD 1600, then concentrated to dryness, taken up with 210 g of n-butanol and stirred for 4 h at 80° C., to obtain 67.5 g of the desired product (0.081 mol).
Yield: 90%

EXAMPLE 7

Alternative method to that described in Example 6
67.1 g (0.089 mol) of 5-(acetylamino)-N,N'-bis(2,3-dihydroxypropyl)-2,4,6-triiodo-1,3-benzenedicarboxamide (prepared as described in Example 4) are dissolved in 178.9 g of water and heated to 85° C. 44.73 ml of 2N NaOH (0.089 mol) and 5.83 g of Ca(OH)$_2$ (0.079 mol) are added at said temperature. After 30 min, a solution of 13.42 g (0.12 mol) of 3-chloro-1,2-propanediol in 79.33 g of water is dropped therein, keeping the same temperature for a further 30 min.

The reaction is quenched with acetic acid until solubilization. After that, the solution is percolated on a ion exchange resin (Amberlite IR120 200 mL, Relite MG1 150 mL, Amberjet 1200 50 mL). The eluate is then percolated on 300 ml of Amberlite XAD 16, then concentrated to dryness, taken up with 210 g of n-butanol and stirred for 4 h at 80° C., to obtain 65.5 g of the desired product (0.078 mol). Yield: 88%

I claim:

1. A process for the preparation of the compound of formula (I), starting from 5-amino-1,3-benzenedicarboxylic acid of formula (II), comprising the steps represented in the following scheme:

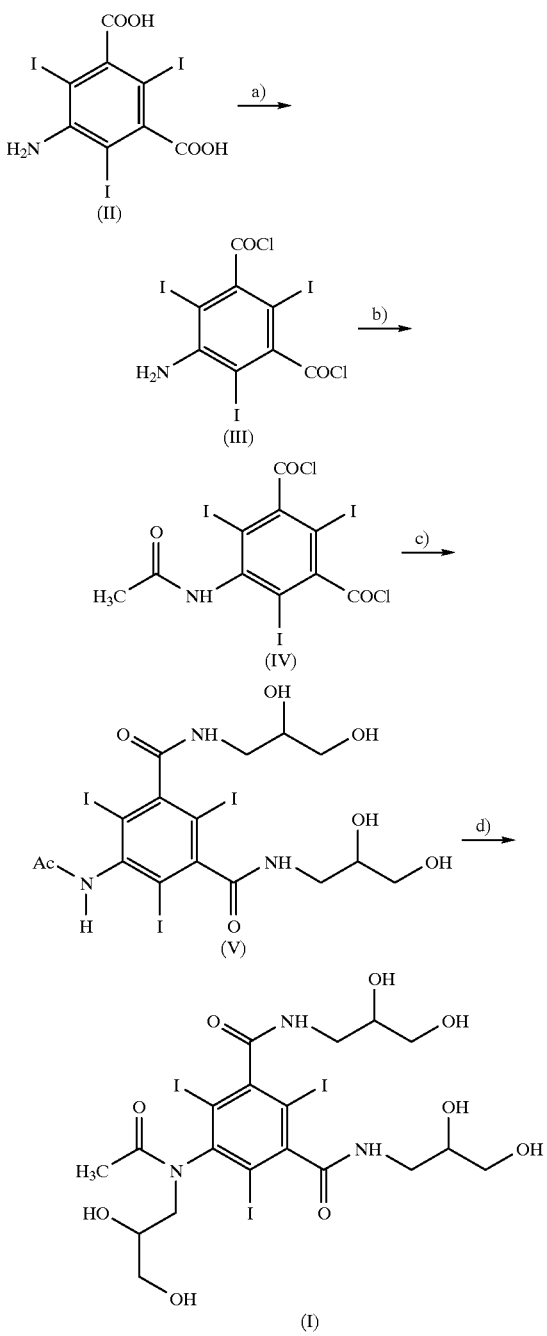

in which step a) is the reaction in heterogeneous phase between 5-amino-2,4,6-triiodo-1,3-benzenedicarboxylic acid and thionyl chloride in a dipolar aprotic solvent selected from the group consisting of straight or branched $C_7$–$C_{16}$ hydrocarbons, $C_7$–$C_8$ aromatic hydrocarbons, 1,1,1-trichloroethane, n-butyl acetate, and diethylene glycol dimethyl ether (diglyme), in the presence of catalytic amounts of a tertiary amine, to give compound (III);

step b) is the acetylation reaction of compound (III) with glacial acetic acid both as the solvent and the reagent and thionyl chloride or the acetylation reaction is with acetyl chloride in a solvent of step (a);

step c) is the formation of compound (V) by reaction of the compound (IV) with 1-amino-2,3-propanediol, by reaction of compound (IV) in a dipolar aprotic solvent, selected from the group consisting of dimethylformamide (DMF), dimethylacetamide (DMA), dimethylsulfoxide (DMSO) and N-methyl-pyrrolidinone;

step d) is the alkylation of compound (V) in aqueous solution at basic pH, by addition of a mixture of sodium hydroxide-calcium hydroxide with 3-chloro-1,2-propanediol or epichlorohydrin, at a temperature of 40–90° C.

2. A process according to claim 1, in which step b) is the acetylation reaction of compound (III) with acetyl chloride in a dipolar aprotic solvent.

3. A process according to claim 1, in which step c) is conducted in the presence of an aliphatic tertiary amine.

4. A process according to claim 1, in which step b) is the acetylation reaction of compound (III) with acetyl chloride in a dipolar aprotic solvent, and step c) is conducted in the presence of an aliphatic tertiary amine.

5. A process according to claim 1, in which, in step a):
the hydrocarbon is selected from the group consisting of straight or branched $C_8$–$C_{14}$ hydrocarbons,
the aromatic hydrocarbon is a methyl-substituted benzene, and
the tertiary amine is selected from the group consisting of N-methyl-morpholine, triethylamine, quinoline, dimethylaminopyridine and 2-ethyl-5-methylpyridine.

6. A process according to claim 1 in which, in step a), diglyme in amounts from 0.5 kg of diglyme/kg of starting product is added to the 5-amino-2,4,6,-triiodo-1,3-benzenedicarboxylic acid chlorination mixture.

7. A process according to claim 1 in which, in step a), n-dodecane and quinoline are used as catalyst.

8. A process according to claim 1 in which, in step b), the reaction temperature ranges from 50–60° C., the amount of AcOH is 40–60 times the moles of compound (III), and thionyl chloride is 2–4 times the moles of compound (III).

9. A process according to claim 2 in which, in step b), the reaction temperature is 0–40° C. and acetyl chloride is added in amounts 1.5–3 times the moles of compound (III).

10. A process according to claim 1 in which, in step c), the amount of isoserinol is 4.2–4.6 times the moles of compound (IV).

11. A process according to claim 3 in which, in step c), the isoserinol amount is 2.05–2.4 times the moles of compound (IV) and the aliphatic tertiary amine, selected from the group of triethylamine, tributylamine, tripropylamine, trimethylamine and N-methyl-morpholine, is present in amounts 2.1–2.5 times the moles of compound (IV).

12. A process according to claim 1 in which the alkylation step d) is carried out in aqueous medium, alkalinized by the addition of a sodium hydroxide-calcium hydroxide mixture, in a sodium hydroxide to compound (V) equimolar ratio and in a calcium hydroxide to compound (V) ratio of 0.5–0.9, while maintaining the reaction at pH 10–12, at a temperature of 40–90° C.

13. A process according to claim 12 in which sodium hydroxide is added to compound (V) suspended in water and kept at a predetermined temperature until complete dissolution, then calcium hydroxide is added, which remains in part as a precipitate, and about 10–20% of the alkylating agent aqueous solution is added at the same temperature.

14. A process according to claim 5 in which the $C_8$–$C_{14}$ hydrocarbon is n-octane, n-decane, n-dodecane, ligroin or kerosene.

15. A process according to claim 5 in which the methyl-substituted benzene is toluene or a xylene.

* * * * *